US012465524B2

(12) United States Patent
Kurihara

(10) Patent No.: US 12,465,524 B2
(45) **Date of Patent: *Nov. 11, 2025**

(54) EAR-WORN DEVICE AND REPRODUCTION METHOD

(71) Applicant: Panasonic Intellectual Property Management Co., Ltd., Osaka (JP)

(72) Inventor: Shinichiro Kurihara, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 456 days.

This patent is subject to a terminal disclaimer.

(21) Appl. No.: 17/925,242

(22) PCT Filed: Jan. 12, 2022

(86) PCT No.: PCT/JP2022/000697
§ 371 (c)(1),
(2) Date: Nov. 14, 2022

(87) PCT Pub. No.: WO2022/259589
PCT Pub. Date: Dec. 15, 2022

(65) Prior Publication Data

US 2023/0320903 A1 Oct. 12, 2023

(30) Foreign Application Priority Data

Jun. 8, 2021 (JP) ................................ 2021-096075

(51) Int. Cl.
*A61F 11/08* (2006.01)
*G10K 11/178* (2006.01)
(Continued)

(52) U.S. Cl.
CPC ............ *A61F 11/08* (2013.01); *G10K 11/178* (2013.01); *G10L 25/84* (2013.01); *H04R 25/00* (2013.01)

(58) Field of Classification Search
CPC ....... A61F 11/08; G10K 11/178; G10L 25/84; H04R 25/00
See application file for complete search history.

(56) References Cited

U.S. PATENT DOCUMENTS 6,285,768 B1 9/2001 Ikeda
9,509,269 B1 * 11/2016 Rosenberg .............. H03G 3/32
(Continued)

FOREIGN PATENT DOCUMENTS

EP 1674061 A1 6/2006
EP 3745736 A1 * 12/2020 ........... G10K 11/175
(Continued)

OTHER PUBLICATIONS

Extended European Search Report dated Sep. 12, 2024 for the counterpart European patent application No. 22800559.1.
(Continued)

*Primary Examiner* — Andrew Sniezek
(74) *Attorney, Agent, or Firm* — Rimon P.C.

(57) ABSTRACT

An ear-worn device includes: a microphone that obtains a sound and outputs a first sound signal of the sound obtained; a DSP that outputs a second sound signal based on the first sound signal, when determining that the sound satisfies a predetermined requirement relating to a noise component contained in the sound and the sound contains human voice; a loudspeaker that outputs a reproduced sound based on the second sound signal output; and a housing that contains the microphone, the DSP, and the loudspeaker.

14 Claims, 13 Drawing Sheets

(51) Int. Cl.

| | |
|---|---|
| ***G10L 25/84*** | (2013.01) |
| ***H04R 25/00*** | (2006.01) |

(56) References Cited

U.S. PATENT DOCUMENTS

| | | | | |
|---|---|---|---|---|
| 2006/0083387 | A1 | 4/2006 | Emoto | |
| 2013/0003983 | A1 | 1/2013 | Hata et al. | |
| 2014/0270200 | A1 * | 9/2014 | Usher | G10L 25/78<br>381/74 |
| 2019/0251955 | A1 | 8/2019 | Degraye et al. | |
| 2020/0382859 | A1 | 12/2020 | Woodruff et al. | |
| 2024/0339101 | A1 * | 10/2024 | Kurihara | H04R 1/10 |

FOREIGN PATENT DOCUMENTS

| | | | |
|---|---|---|---|
| JP | 11-345000 | A | 12/1999 |
| JP | 2006-093792 | A | 4/2006 |
| JP | 2011-199699 | A | 10/2011 |
| JP | 2012-249184 | A | 12/2012 |
| JP | 2021-511755 | A | 5/2021 |
| WO | 2019/111050 | A1 | 6/2019 |

OTHER PUBLICATIONS

International Search Report issued on Apr. 19, 2022 in International Patent Application No. PCT/JP2022/000697.

* cited by examiner

Announcement sound output during movement

No announcement sound output during movement

Announcement sound output during stop

Power spectrogram

No announcement sound output during stop

Power spectrogram

EAR-WORN DEVICE AND REPRODUCTION METHOD

CROSS-REFERENCE OF RELATED APPLICATIONS

This application is the U.S. National Phase under 35 U.S.C. § 371 of International Patent Application No. PCT/JP2022/000697, filed on Jan. 12, 2022, which in turn claims the benefit of Japanese Patent Application No. 2021-096075, filed on Jun. 8, 2021, the entire disclosures of which Applications are incorporated by reference herein.

TECHNICAL FIELD

The present disclosure relates to an ear-worn device and a reproduction method.

BACKGROUND ART

Various techniques for ear-worn devices such as earphones and headphones have been proposed. Patent Literature (PTL) 1 discloses a technique for speech reproduction headphones.

CITATION LIST

Patent Literature

[PTL 1]
Japanese Unexamined Patent Application Publication No. 2006-093792

SUMMARY OF INVENTION

Technical Problem

The present disclosure provides an ear-worn device that can reproduce human voice heard in the surroundings according to the ambient noise environment.

Solution to Problem

An ear-worn device according to an aspect of the present disclosure includes: a microphone that obtains a sound and outputs a first sound signal of the sound obtained; a signal processing circuit that outputs a second sound signal based on the first sound signal, when determining that the sound satisfies a predetermined requirement relating to a noise component contained in the sound and the sound contains human voice; a loudspeaker that outputs a reproduced sound based on the second sound signal output; and a housing that contains the microphone, the signal processing circuit, and the loudspeaker.

Advantageous Effects of Invention

The ear-worn device according to an aspect of the present disclosure can reproduce human voice heard in the surroundings according to the ambient noise environment.

DESCRIPTION OF EMBODIMENTS

Figure 1:
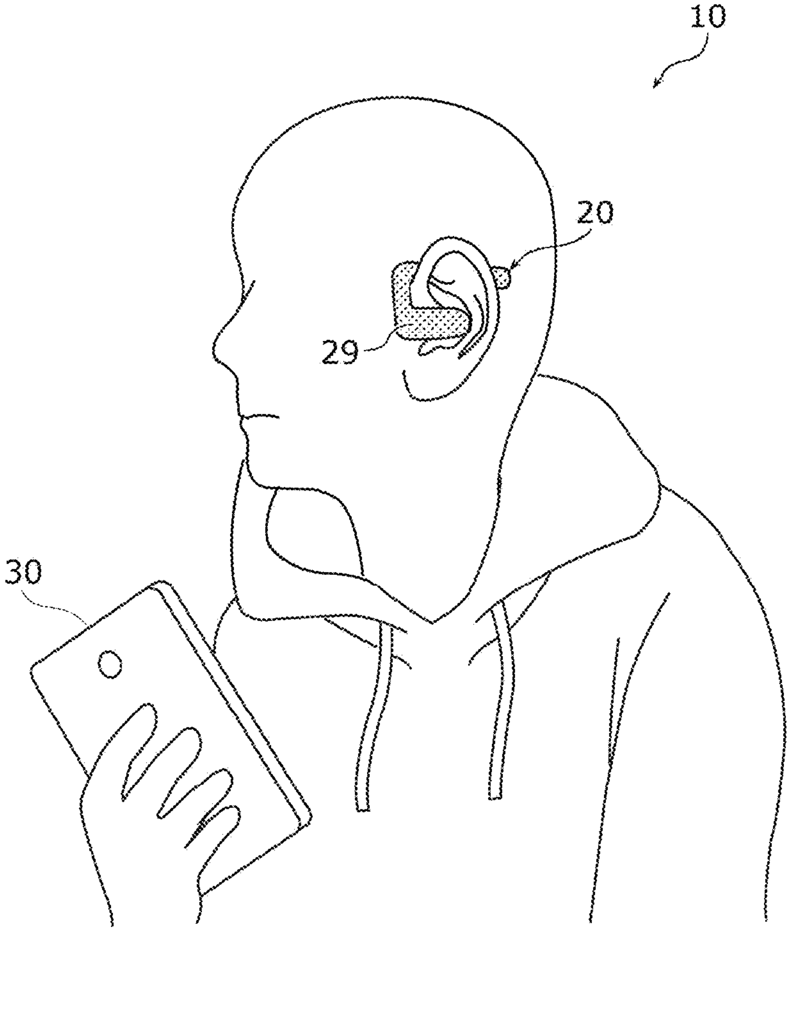
FIG. 1 is an external view of a device included in a sound signal processing system according to an embodiment.

An embodiment will be described in detail below, with reference to the drawings. The embodiment described below shows a general or specific example. The numerical values, shapes, materials, structural elements, the arrangement and connection of the structural elements, steps, the order of steps, etc. shown in the following embodiment are mere examples, and do not limit the scope of the present disclosure. Of the structural elements in the embodiment described below, the structural elements not recited in any one of the independent claims are described as optional structural elements.

Each drawing is a schematic, and does not necessarily provide precise depiction. In the drawings, structural elements that are substantially the same are given the same reference marks, and repeated description may be omitted or simplified.

Embodiment

[Structure]

Figure 2:
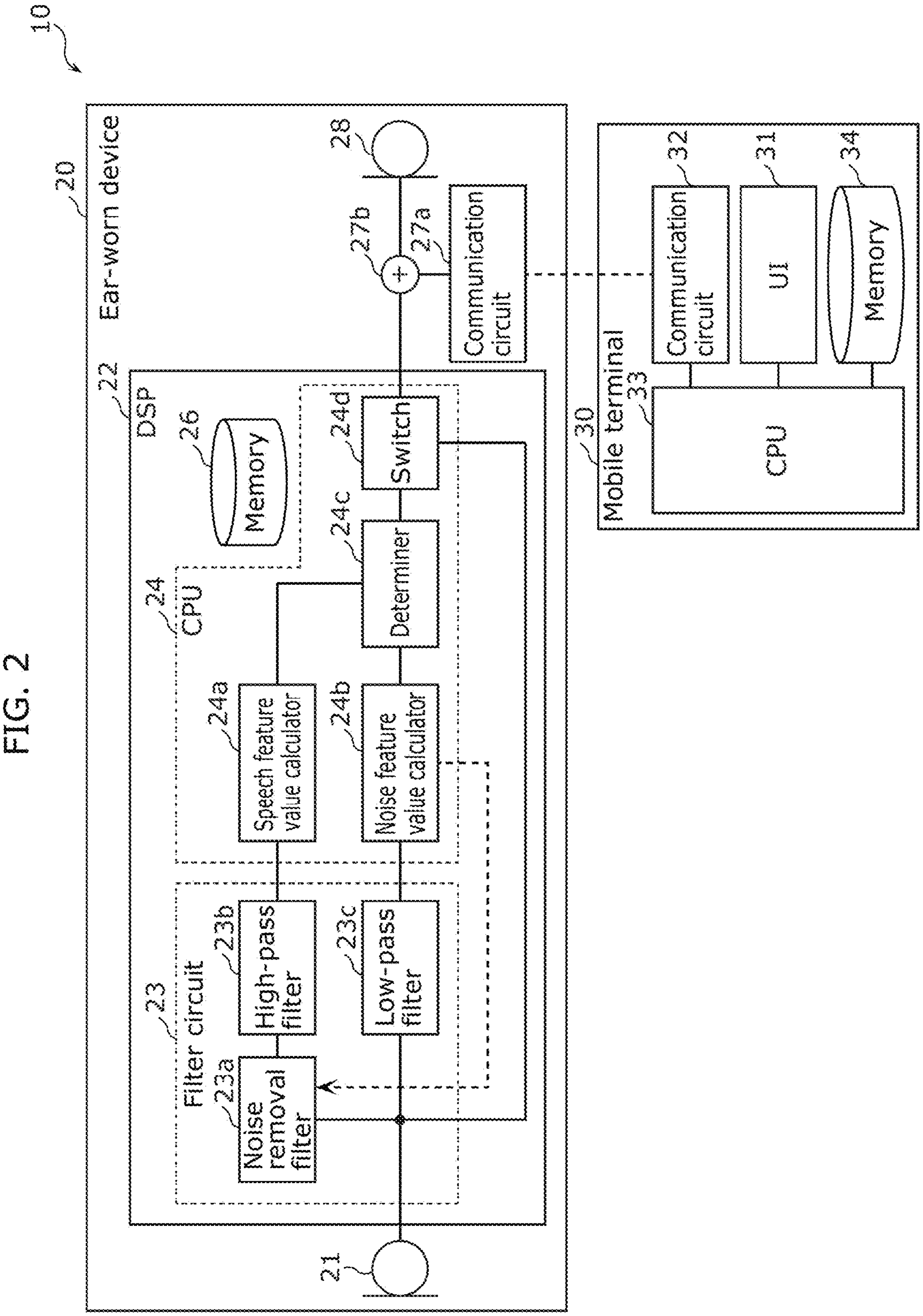
FIG. 2 is a block diagram illustrating the functional structure of the sound signal processing system according to the embodiment.

The structure of a sound signal processing system according to an embodiment will be described below. FIG. 1 is an external view of a device included in the sound signal processing system according to the embodiment. FIG. 2 is a block diagram illustrating the functional structure of the sound signal processing system according to the embodiment.

As illustrated in FIG. 1 and FIG. 2, sound signal processing system 10 according to the embodiment includes ear-worn device 20 and mobile terminal 30. First, ear-worn device 20 will be described below.

Ear-worn device 20 is an earphone-type device that reproduces a fourth sound signal provided from mobile terminal 30. The fourth sound signal is, for example, a sound signal of music content. Ear-worn device 20 has an external sound capture function (also referred to as "external sound capture mode") of capturing a sound around the user (i.e. ambient sound) during the reproduction of the fourth sound signal.

Herein, the "ambient sound" is, for example, an announcement sound. For example, the announcement sound is a sound output, in a mobile body such as a train, a bus, or an airplane, from a loudspeaker installed in the mobile body. The announcement sound contains human voice.

Ear-worn device 20 operates in a normal mode in which the fourth sound signal provided from mobile terminal 30 is reproduced, and the external sound capture mode in which a sound around the user is captured and reproduced. For example, in the case where, when the user wearing ear-worn device 20 is on a moving mobile body and is listening to music content in the normal mode, an announcement sound is output in the mobile body and the output announcement sound contains human voice, ear-worn device 20 automatically transitions from the normal mode to the external sound capture mode. This prevents the user from missing the announcement sound.

Specifically, ear-worn device 20 includes microphone 21, DSP 22, communication circuit 27*a*, mixing circuit 27*b*, and loudspeaker 28. Communication circuit 27*a* and mixing circuit 27*b* may be included in DSP 22. Microphone 21, DSP 22, communication circuit 27*a*, mixing circuit 27*b*, and loudspeaker 28 are contained in housing 29 (illustrated in FIG. 1).

Microphone 21 is a sound pickup device that obtains a sound around ear-worn device 20 and outputs a first sound signal based on the obtained sound. Non-limiting specific examples of microphone 21 include a condenser microphone, a dynamic microphone, and a microelectromechanical systems (MEMS) microphone. Microphone 21 may be omnidirectional or may have directivity.

DSP 22 performs signal processing on the first sound signal output from microphone 21 to realize the external sound capture function. For example, DSP 22 realizes the external sound capture function by outputting a second sound signal based on the first sound signal to loudspeaker 28. DSP 22 also has a noise canceling function, and can output a third sound signal obtained by performing phase inversion processing on the first sound signal. DSP 22 is an example of a signal processing circuit. Specifically, DSP 22 includes filter circuit 23, central processing unit (CPU) 24, and memory 26.

Filter circuit 23 includes noise removal filter 23*a*, high-pass filter 23*b*, and low-pass filter 23*c*. Noise removal filter 23*a* is a filter for removing noise contained in the first sound signal output from microphone 21. Noise removal filter 23*a* is, for example, a nonlinear digital filter, but may be a filter using a spectral subtraction method that removes noise in a frequency domain. Noise removal filter 23*a* may be a Wiener filter.

High-pass filter 23*b* attenuates a component in a band of 512 Hz or less contained in the noise-removed first sound signal output from noise removal filter 23*a*. Low-pass filter 23*c* attenuates a component in a band of 512 Hz or more contained in the first sound signal output from microphone 21. These cutoff frequencies are examples, and the cutoff frequencies may be determined empirically or experimentally. For example, the cutoff frequencies are determined according to the type of the mobile body in which ear-worn device 20 is expected to be used.

CPU 24 includes speech feature value calculator 24*a*, noise feature value calculator 24*b*, determiner 24*c*, and switch 24*d* as functional structural elements. The functions of speech feature value calculator 24*a*, noise feature value calculator 24*b*, determiner 24*c*, and switch 24*d* are implemented, for example, by CPU 24 executing a computer program stored in memory 26. The functions of speech feature value calculator 24*a*, noise feature value calculator 24*b*, determiner 24*c*, and switch 24*d* will be described in detail later.

Memory 26 is a storage device that stores the computer program executed by CPU 24, various information necessary for implementing the external sound capture function, and the like. Memory 26 is implemented by semiconductor memory or the like. Memory 26 may be implemented not as internal memory of DSP 22 but as external memory of DSP 22.

Communication circuit 27*a* receives the fourth sound signal from mobile terminal 30. Communication circuit 27*a* is, for example, a wireless communication circuit, and communicates with mobile terminal 30 based on a communication standard such as Bluetooth® or Bluetooth® Low Energy (BLE).

Mixing circuit 27*b* mixes the second sound signal or the third sound signal output from DSP 22 with the fourth sound signal received by communication circuit 27*a*, and outputs the mixed sound signal to loudspeaker 28. Communication circuit 27*a* and mixing circuit 27*b* may be implemented as one system-on-a-chip (SoC).

Loudspeaker 28 outputs a reproduced sound based on the mixed sound signal obtained from mixing circuit 27*b*. Loudspeaker 28 is a loudspeaker that emits sound waves toward the earhole (eardrum) of the user wearing ear-worn device 20. Alternatively, loudspeaker 28 may be a bone-conduction loudspeaker.

Next, mobile terminal 30 will be described below. Mobile terminal 30 is an information terminal that functions as a user interface device in sound signal processing system 10 as a result of a predetermined application program being installed therein. Mobile terminal 30 also functions as a sound source that provides the fourth sound signal (music content) to ear-worn device 20. By operating mobile terminal 30, the user can, for example, select music content reproduced by loudspeaker 28 and switch the operation mode of ear-worn device 20. Mobile terminal 30 includes user interface (UI) 31, communication circuit 32, CPU 33, and memory 34.

UI 31 is a user interface device that receives operations by the user and presents images to the user. UI 31 is implemented by an operation receiver such as a touch panel and a display such as a display panel.

Communication circuit 32 transmits the fourth sound signal which is a sound signal of music content selected by the user, to ear-worn device 20. Communication circuit 32 is, for example, a wireless communication circuit, and communicates with ear-worn device 20 based on a communication standard such as Bluetooth® or Bluetooth® Low Energy (BLE).

CPU 33 performs information processing relating to displaying an image on the display, transmitting the fourth sound signal using communication circuit 32, etc. CPU 33 is, for example, implemented by a microcomputer. Alternatively, CPU 33 may be implemented by a processor. The image display function, the fourth sound signal transmission function, and the like are implemented by CPU 33 executing a computer program stored in memory 34.

Memory 34 is a storage device that stores various information necessary for CPU 33 to perform information processing, the computer program executed by CPU 33, the fourth sound signal (music content), and the like. Memory 34 is, for example, implemented by semiconductor memory.

Example 1

Figure 3:
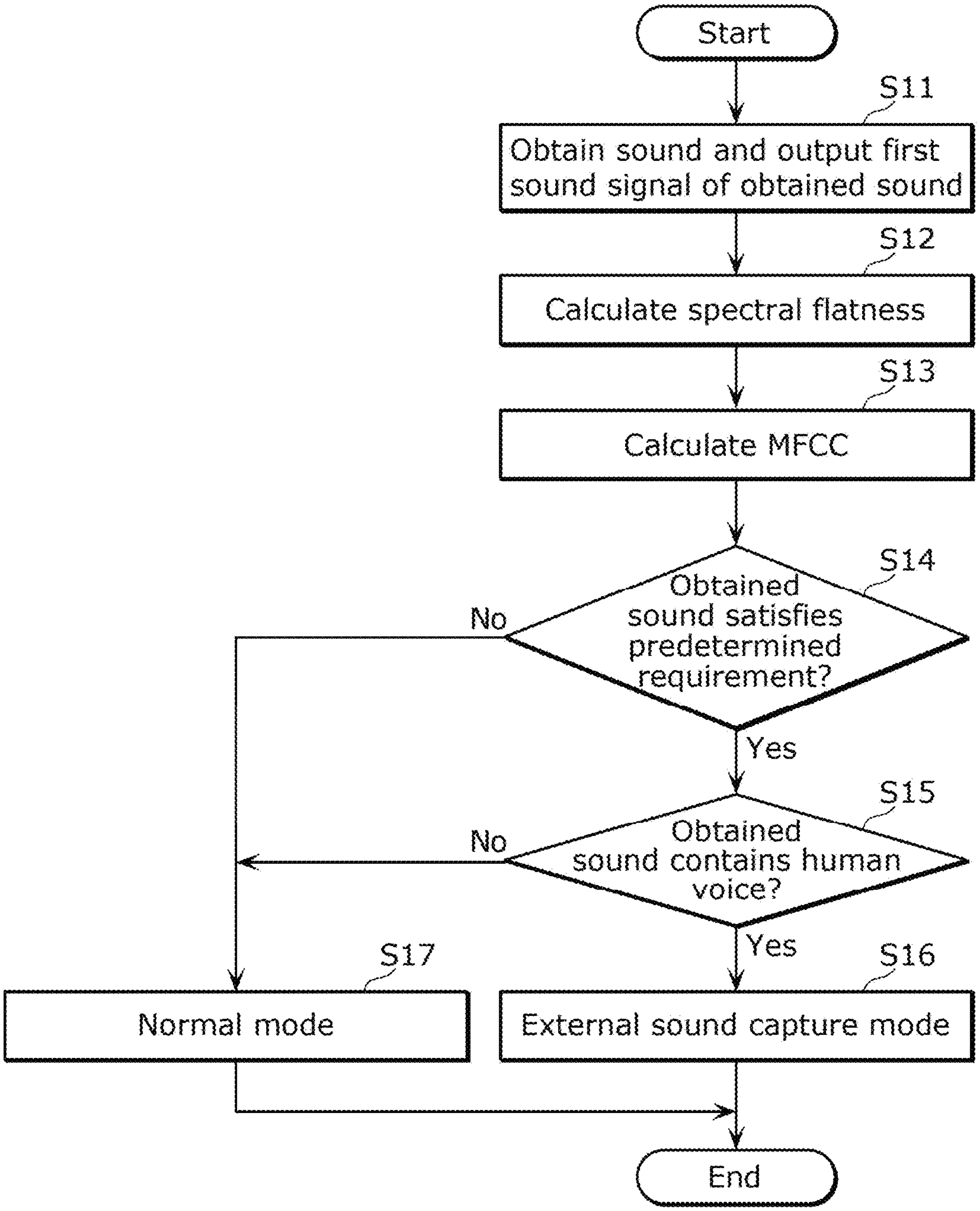
FIG. 3 is a flowchart of Example 1 of an ear-worn device according to the embodiment.

As mentioned above, ear-worn device 20 can automatically operate in the external sound capture mode, when the mobile body the user is on is moving and an announcement sound is output in the mobile body. A plurality of examples of ear-worn device 20 will be described below, taking specific situations as examples. First, Example 1 of ear-worn device 20 will be described below. FIG. 3 is a flowchart of Example 1 of ear-worn device 20. Example 1 is an example of operation when the user wearing ear-worn device 20 is on a mobile body.

Microphone 21 obtains a sound, and outputs a first sound signal of the obtained sound (S11). Noise feature value calculator 24*b* performs signal processing on the first sound signal output from microphone 21 and undergone filtering by low-pass filter 23*c*, to calculate spectral flatness (S12). The spectral flatness is an example of a feature value of noise contained in the first sound signal, and specifically a feature value indicating the flatness of the signal. The spectral flatness indicates, for example, how close the first sound signal is to noise such as white noise, pink noise, or brown noise. In the case where the cutoff frequency of low-pass filter 23*c* is 512 Hz, the spectral flatness calculated in Step S12 indicates the flatness of noise of 512 Hz or less.

Let $S_k$ be the complex spectrum of the first sound signal to which low-pass filter 23*c* is applied, and $N_{FFT}$ be the number of frequency bins of Fourier transform (in other words, the number of FFT calculation points, the number of sampling points). Spectral flatness $S_F$ is calculated according to the following formula. Here, exp[x] denotes e to the power of x, and In(x) denotes $\log_e(x)$. In the following formula, the numerator on the right side corresponds to calculation of entropy, and the denominator on the right side corresponds to calculation for normalizing the entropy.

$$S_F = \frac{\exp\left[\frac{2}{N_{FFT}}\sum_{k=1}^{N_{FFT}/2}\ln|S_k|^2\right]}{\frac{2}{N_{FFT}}\sum_{k=1}^{N_{FFT}/2}|S_k|^2} \quad \text{[Math. 1]}$$

Following this, speech feature value calculator 24*a* performs signal processing on the first sound signal output from microphone 21 and undergone filtering by noise removal filter 23*a* and high-pass filter 23*b*, to calculate a mel-frequency cepstral coefficient (MFCC) (S13). The MFCC is a cepstral coefficient used as a feature value in speech recognition and the like, and is obtained by converting a power spectrum compressed using a mel-filter bank into a logarithmic power spectrum and applying an inverse discrete cosine transform to the logarithmic power spectrum. Speech feature value calculator 24*a* outputs the calculated MFCC to determiner 24*c*.

Following this, determiner 24*c* determines whether the sound obtained by microphone 21 satisfies a predetermined requirement relating to a noise component contained in the sound (S14). Specifically, determiner 24*c* determines whether the value of spectral flatness $S_F$ output from noise feature value calculator 24*b* is greater than or equal to a threshold.

Spectral flatness $S_F$ takes a value from 0 to 1. When the value is closer to 1, it is assumed that noise closer to white noise is obtained by microphone 21. That is, when the value of spectral flatness $S_F$ is greater than or equal to the threshold, it is assumed that the mobile body the user is on is moving. In other words, Step S14 is a step of determining whether the mobile body is moving.

In the case where the value of spectral flatness $S_F$ is greater than or equal to the threshold in Step S14, determiner 24*c* determines that the sound obtained by microphone 21 satisfies the predetermined requirement (S14: Yes), and performs the process in Step S15. Determiner 24*c* determines whether the sound obtained by microphone 21 contains human voice, based on the MFCC output from speech feature value calculator 24*a* (S15).

For example, determiner 24*c* includes a machine learning model (neural network) that receives the MFCC as input and outputs a determination result of whether the sound contains human voice, and determines whether the sound obtained by microphone 21 contains human voice using the machine learning model. The human voice herein is assumed to be human voice contained in an announcement sound.

In the case where determiner 24*c* determines that the sound obtained by microphone 21 contains human voice (S15: Yes), switch 24*d* operates in the external sound capture mode (S16). That is, when the mobile body is moving (S14: Yes) and human voice is output (S15: Yes), ear-worn device 20 (switch 24*d*) operates in the external sound capture mode (S16).

Figure 4:
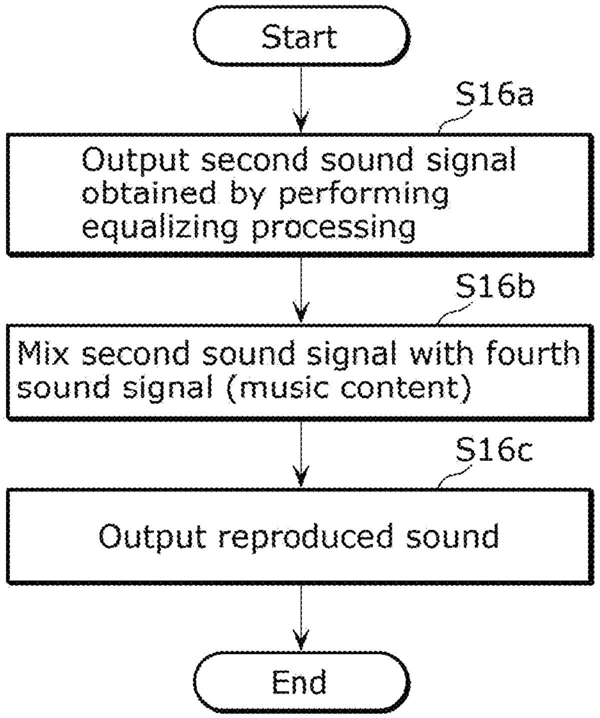
FIG. 4 is a first flowchart of the operation of the ear-worn device according to the embodiment in an external sound capture mode.

FIG. 4 is a first flowchart of operation in the external sound capture mode. In the external sound capture mode, switch 24*d* generates a second sound signal by performing equalizing processing for enhancing a specific frequency component on the first sound signal output from microphone 21, and outputs the generated second sound signal (S16*a*). For example, the specific frequency component is a frequency component of 100 Hz or more and 2 kHz or less. By enhancing the band corresponding to the frequency band of human voice in this way, human voice is enhanced. Thus, the announcement sound (more specifically, the human voice contained in the announcement sound) is enhanced.

Mixing circuit 27*b* mixes the second sound signal with the fourth sound signal (music content) received by communication circuit 27*a*, and outputs the resultant sound signal to loudspeaker 28 (S16*b*). Loudspeaker 28 outputs a reproduced sound based on the second sound signal mixed with the fourth sound signal (S16*c*). Since the announcement sound is enhanced as a result of the process in Step S16*a*, the user of ear-worn device 20 can easily hear the announcement sound.

In the case where determiner 24*c* determines that the sound obtained by microphone 21 does not satisfy the predetermined requirement (i.e. the value of spectral flatness $S_F$ is less than the threshold) (S14 in FIG. 3: No) and in the case where determiner 24*c* determines that the sound does not contain human voice (S14: Yes, and S15: No), switch 24*d* operates in the normal mode (S17). Loudspeaker 28 outputs the reproduced sound (music content) of the fourth sound signal received by communication circuit 27*a*, and does not output the reproduced sound based on the second sound signal. That is, switch 24*d* causes loudspeaker 28 not to output the reproduced sound based on the second sound signal.

The above-described process illustrated in the flowchart in FIG. 3 is repeatedly performed at predetermined time intervals. That is, which of the normal mode and the external sound capture mode ear-worn device 20 is to operate in is determined at predetermined time intervals. The predetermined time interval is, for example, 1/60 seconds. Only in the case where the condition that the mobile body is moving and human voice is output is satisfied (i.e. Step S14: Yes, and Step S15: Yes), ear-worn device 20 operates in the external sound capture mode. Otherwise, ear-worn device 20 operates in the normal mode.

As described above, in the case where DSP 22 determines that the noise contained in the sound obtained by microphone 21 satisfies the predetermined requirement and the sound contains human voice, DSP 22 outputs the second sound signal based on the first sound signal. In the case where DSP 22 determines that the sound obtained by microphone 21 satisfies the predetermined requirement relating to the noise component contained in the sound and the sound contains human voice, DSP 22 outputs the second sound signal obtained by performing signal processing on the first sound signal. The signal processing includes equalizing processing for enhancing the specific frequency component of the sound. In the case where DSP 22 determines that the sound obtained by microphone 21 does not satisfy the predetermined requirement and in the case where DSP 22 determines that the sound does not contain human voice, DSP 22 causes loudspeaker 28 not to output the reproduced sound based on the second sound signal.

Thus, ear-worn device 20 can assist the user who is on the mobile body in hearing the announcement sound while the mobile body is moving. The user is unlikely to miss the announcement sound even when immersed in the music content.

The operation in the external sound capture mode is not limited to the operation illustrated in FIG. 4. For example, the equalizing processing in Step S16*a* is not essential, and the second sound signal may be generated by performing signal processing of increasing the gain (amplitude) of the first sound signal. Moreover, it is not essential to perform signal processing on the first sound signal in the external sound capture mode.

Figure 5:
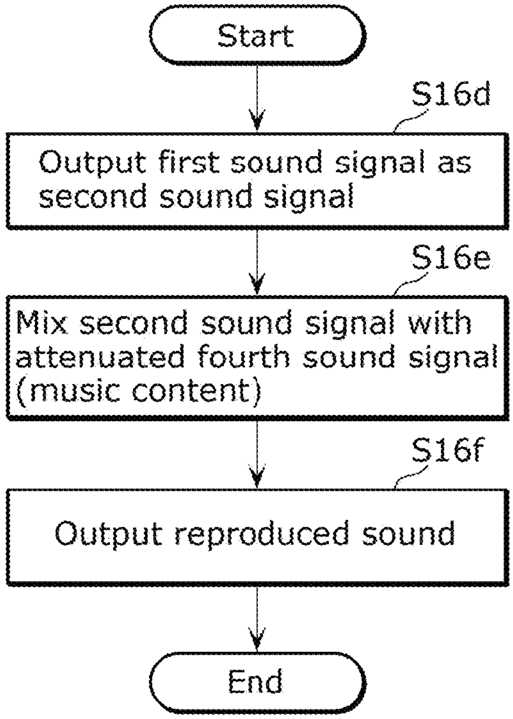
FIG. 5 is a second flowchart of the operation of the ear-worn device according to the embodiment in the external sound capture mode.

FIG. 5 is a second flowchart of operation in the external sound capture mode. In the example in FIG. 5, switch 24*d* outputs the first sound signal output from microphone 21, as the second sound signal (S16*d*). That is, switch 24*d* outputs substantially the first sound signal itself as the second sound signal. Switch 24*d* also instructs mixing circuit 27*b* to attenuate (i.e. gain decrease, amplitude attenuation) the fourth sound signal in the mixing.

Mixing circuit 27*b* mixes the second sound signal with the fourth sound signal (music content) attenuated in amplitude to be lower than in the normal mode, and outputs the resultant sound signal to loudspeaker 28 (S16*e*). Loudspeaker 28 outputs a reproduced sound based on the second sound signal mixed with the fourth sound signal attenuated in amplitude (S16*f*).

Thus, in the external sound capture mode after DSP 22 starts outputting the second sound signal, the second sound signal may be mixed with the fourth sound signal attenuated in amplitude to be lower than in the normal mode before DSP 22 starts outputting the second sound signal. Consequently, the announcement sound is enhanced, so that the user of ear-worn device 20 can easily hear the announcement sound.

The operation in the external sound capture mode is not limited to the operations illustrated in FIG. 4 and FIG. 5. For example, in the operation in the external sound capture mode in FIG. 4, the second sound signal generated by performing equalizing processing on the first sound signal may be mixed with the attenuated fourth sound signal as in Step S16*e* in FIG. 5. In the operation in the external sound capture mode in FIG. 5, the process of attenuating the fourth sound signal may be omitted and the second sound signal may be mixed with the unattenuated fourth sound signal.

Example 2

Ear-worn device 20 may have a noise canceling function (hereafter also referred to as "noise canceling mode") of reducing environmental sound around the user wearing ear-worn device 20 during the reproduction of the fourth sound signal (music content).

First, the noise canceling mode will be described below. When the user performs an operation of instructing UI 31 in mobile terminal 30 to set the noise canceling mode, CPU 33 transmits a setting command for setting the noise canceling mode in ear-worn device 20, to ear-worn device 20 using communication circuit 32. Once communication circuit 27*a* in ear-worn device 20 has received the setting command, switch 24*d* operates in the noise canceling mode.

Figure 6:
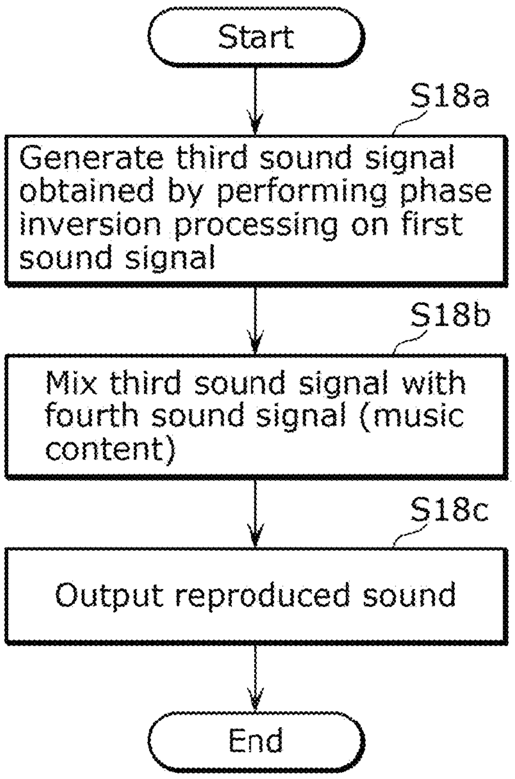
FIG. 6 is a flowchart of the operation of the ear-worn device according to the embodiment in a noise canceling mode.

FIG. 6 is a flowchart of operation in the noise canceling mode. In the noise canceling mode, switch 24*d* performs phase inversion processing on the first sound signal output from microphone 21, and outputs the resultant sound signal as the third sound signal (S18*a*).

Mixing circuit 27*b* mixes the third sound signal with the fourth sound signal (music content) received by communication circuit 27*a*, and outputs the resultant sound signal (S18*b*). Loudspeaker 28 outputs a reproduced sound based on the third sound signal mixed with the fourth sound signal (S18*c*). Since it sounds to the user of ear-worn device 20 that the sound around ear-worn device 20 has been attenuated as a result of the processes in Steps S18*a* and S18*b*, the user can clearly hear the music content.

Figure 7:
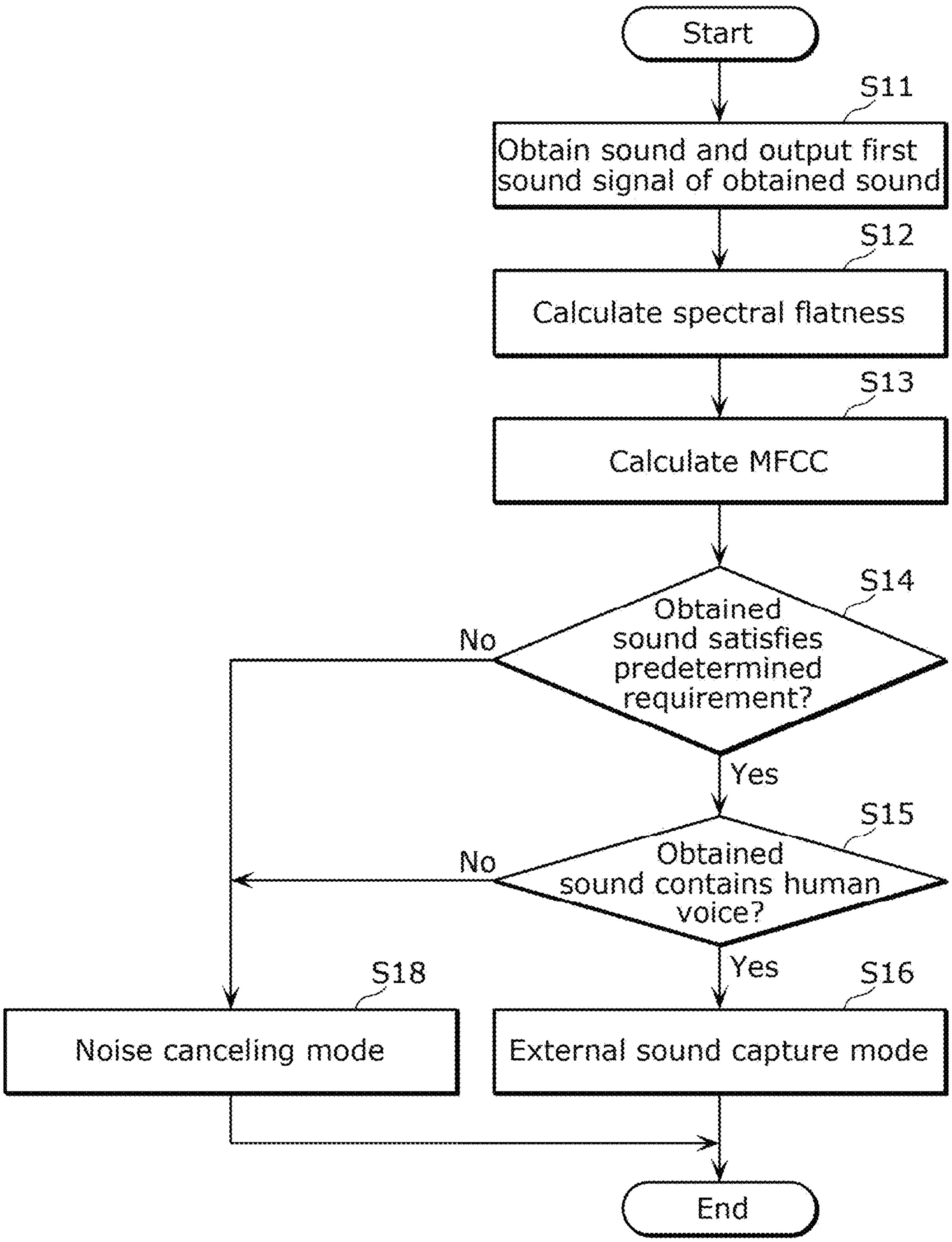
FIG. 7 is a flowchart of Example 2 of the ear-worn device according to the embodiment.

Example 2 in which ear-worn device 20 operates in the noise canceling mode instead of the normal mode will be described below. FIG. 7 is a flowchart of Example 2 of ear-worn device 20. Example 2 is an example of operation when the user wearing ear-worn device 20 is on a mobile body.

The processes in Steps S11 to S13 in FIG. 7 are the same as the processes in Steps S11 to S13 in Example 1 (FIG. 3).

Following Step S13, determiner 24*c* determines whether the sound obtained by microphone 21 satisfies a predetermined requirement relating to a noise component contained in the sound (S14). The details of the process in Step S14 are the same as those of Step S14 in Example 1 (FIG. 3). Specifically, determiner 24*c* determines whether the value of spectral flatness $S_F$ is greater than or equal to a threshold.

In the case where the value of spectral flatness $S_F$ is greater than or equal to the threshold in Step S14, determiner 24*c* determines that the sound obtained by microphone 21 satisfies the predetermined requirement (S14: Yes), and performs the process in Step S15. Determiner 24*c* determines whether the sound obtained by microphone 21 contains human voice, based on the MFCC output from speech feature value calculator 24*a* (S15). The details of the process in Step S15 are the same as those of Step S15 in Example 1 (FIG. 3).

In the case where determiner 24*c* determines that the sound obtained by microphone 21 contains human voice (S15: Yes), switch 24*d* operates in the external sound capture mode (S16). That is, when the mobile body is moving (S14: Yes) and human voice is output (S15: Yes), ear-worn device 20 (switch 24*d*) operates in the external sound capture mode (S16). The operation in the external sound capture mode is as described above with reference to FIG. 4, FIG. 5, etc. Since the announcement sound is enhanced as a result of the operation in the external sound capture mode, the user of ear-worn device 20 can easily hear the announcement sound.

In the case where determiner 24*c* determines that the sound obtained by microphone 21 does not satisfy the predetermined requirement (i.e. the value of spectral flatness $S_F$ is less than the threshold) (S14: No) and in the case where determiner 24*c* determines that the sound does not contain human voice (S14: Yes, and S15: No), switch 24*d* operates in the noise canceling mode (S18). The operation in the noise canceling mode is as described above with reference to FIG. 6.

The above-described process illustrated in the flowchart in FIG. 7 is repeatedly performed at predetermined time intervals. That is, which of the noise canceling mode and the external sound capture mode ear-worn device 20 is to operate in is determined at predetermined time intervals. The predetermined time interval is, for example, 1/60 seconds. Only in the case where the condition that the mobile body is moving and human voice is output is satisfied (i.e. Step S14: Yes, and Step S15: Yes), ear-worn device 20 operates in the external sound capture mode. Otherwise, ear-worn device 20 operates in the noise canceling mode.

Thus, in the case where DSP 22 determines that the sound obtained by microphone 21 does not satisfy the predetermined requirement relating to the noise component contained in the sound and in the case where DSP 22 determines that the sound does not contain human voice, DSP 22 outputs the third sound signal obtained by performing phase inversion processing on the first sound signal. Loudspeaker 28 outputs a reproduced sound based on the output third sound signal.

Hence, ear-worn device 20 can assist the user who is on the mobile body in clearly hearing the music content while the mobile body is moving.

Figure 8:
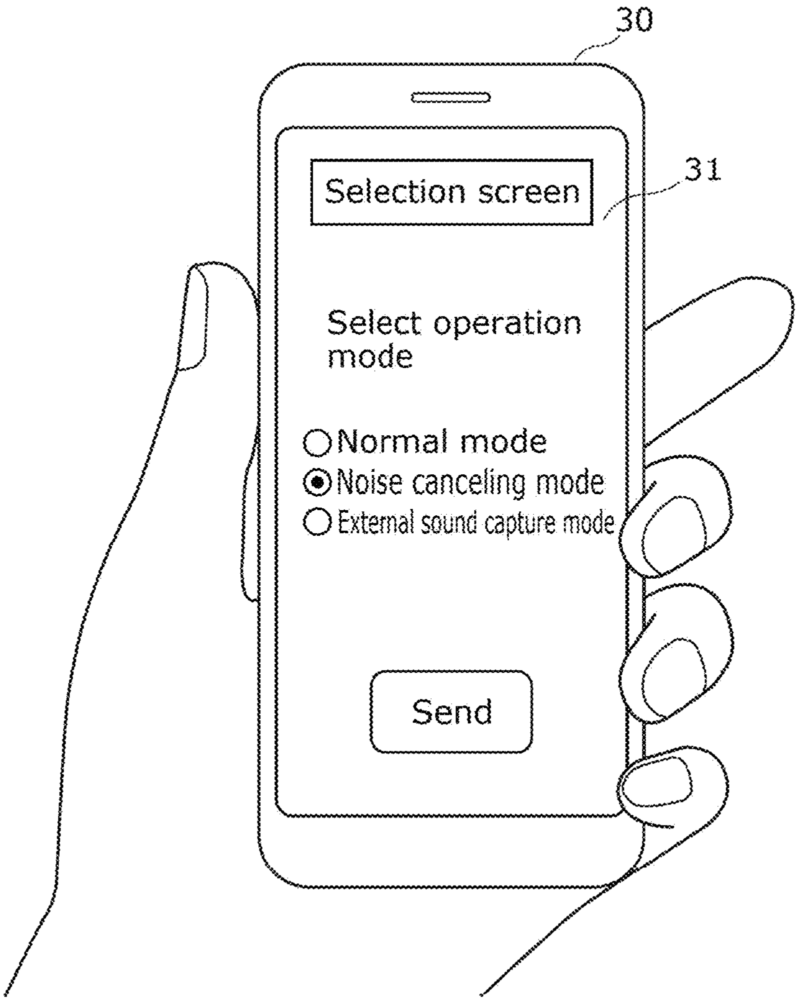
FIG. 8 is a diagram illustrating an example of an operation mode selection screen.

In the case where the user instructs UI 31 in mobile terminal 30 to set the noise canceling mode, for example, a selection screen illustrated in FIG. 8 is displayed on UI 31. FIG. 8 is a diagram illustrating an example of an operation mode selection screen. As illustrated in FIG. 8, the operation modes selectable by the user include, for example, the three modes of the normal mode, the noise canceling mode, and the external sound capture mode. That is, ear-worn device 20 may operate in the external sound capture mode based on operation on mobile terminal 30 by the user.

Example 3

Figure 9:
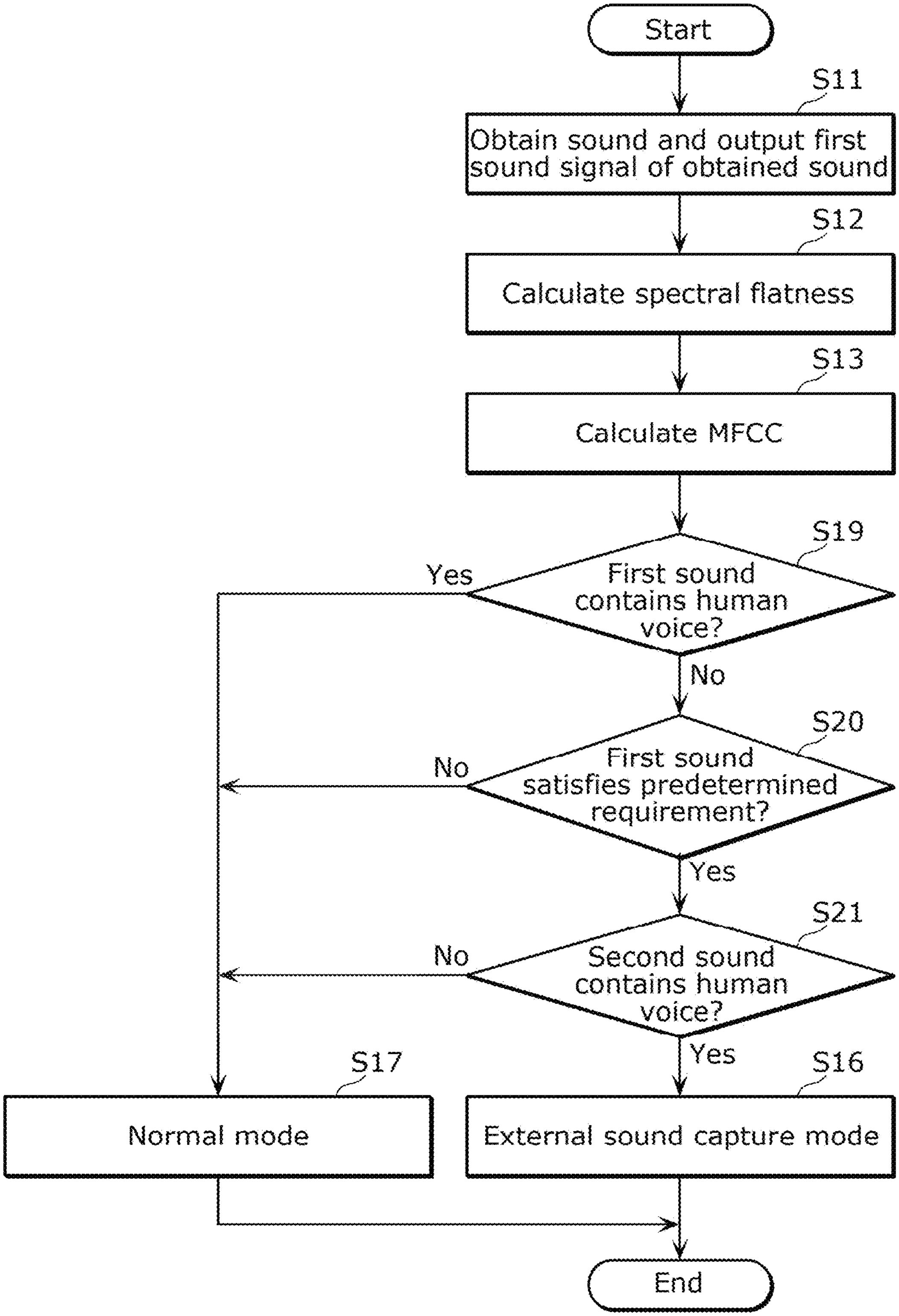
FIG. 9 is a flowchart of Example 3 of the ear-worn device according to the embodiment.

Ear-worn device 20 may determine whether the noise satisfies the predetermined requirement (i.e. whether the mobile body is moving) based on spectral flatness $S_F$ calculated using a part of the first signal containing no human voice. FIG. 9 is a flowchart of Example 3 of ear-worn device 20.

Example 3 is an example of operation when the user wearing ear-worn device 20 is on a mobile body. In Example 3, the first sound signal includes a part corresponding to a first period and a part corresponding to a second period after the first period. The first period corresponds to a first partial signal (i.e. part of the first sound signal) indicating a first sound, and the second period corresponds to a second partial signal (i.e. another part of the first sound signal) indicating a second sound. For example, the second period is a certain period immediately after the first period.

The processes in Steps S11 to S13 are the same as the processes in Steps S11 to S13 in Example 1 (FIG. 3).

Following Step S34, determiner 24*c* determines whether the first sound obtained by microphone 21 contains human voice, based on the MFCC output from speech feature value calculator 24*a* (S19).

In the case where determiner 24*c* determines that the first sound obtained by microphone 21 does not contain human voice (S19: No), determiner 24*c* determines whether the first sound obtained by microphone 21 satisfies a predetermined requirement relating to a noise component contained in the first sound (S20). Specifically, determiner 24*c* determines whether the value of flatness $S_F$ is greater than or equal to a threshold.

In the case where the value of spectral flatness $S_F$ is greater than or equal to the threshold in Step S20, determiner 24*c* determines that the first sound obtained by microphone 21 satisfies the predetermined requirement (S20: Yes), and performs the process in Step S21. Determiner 24*c* determines whether the second sound obtained by microphone 21 contains human voice, based on the MFCC output from speech feature value calculator 24*a* (S21).

In the case where determiner 24*c* determines that the second sound obtained by microphone 21 contains human voice (S21: Yes), switch 24*d* operates in the external sound capture mode (S16). The operation in the external sound capture mode is as described above with reference to FIG. 4, FIG. 5, etc. Since the announcement sound is enhanced as a result of the operation in the external sound capture mode, the user of ear-worn device 20 can easily hear the announcement sound.

In the case where determiner 24*c* determines that the first sound contains human voice (S19: Yes), in the case where determiner 24*c* determines that the first sound does not satisfy the predetermined requirement (i.e. the value of spectral flatness $S_F$ is less than the threshold) (S20: No), and in the case where determiner 24*c* determines that the second sound does not contain human voice (S20: Yes, and S21: No), switch 24*d* operates in the normal mode (S17). Alternatively, the operation in the noise canceling mode in Step S18 described above may be performed instead of Step S17. The operation in the noise canceling mode is as described above with reference to FIG. 6.

The above-described process illustrated in the flowchart in FIG. 9 is repeatedly performed at predetermined time intervals. That is, which of the normal mode and the external sound capture mode ear-worn device 20 is to operate in is determined at predetermined time intervals. The predetermined time interval is, for example, 1/60 seconds. Only in the case where the condition that the mobile body is moving and human voice is output is satisfied (i.e. Step S20: Yes, and Step S21: Yes), ear-worn device 20 operates in the external sound capture mode. Otherwise, ear-worn device 20 operates in the normal mode.

Thus, in the case where DSP 22 determines that the first sound satisfies the predetermined requirement relating to the noise component contained in the first sound, the first sound does not contain human voice, and the second sound contains human voice, DSP 22 outputs the second sound signal.

Since ear-worn device 20 determines whether the noise satisfies the predetermined requirement using the part of the first sound signal containing no human voice, the determination accuracy can be improved.

[Supplementary Remarks on Determination of Whether Noise Satisfies Predetermined Requirement]

In the foregoing embodiment, determiner 24*c* determines whether the noise satisfies the predetermined requirement (i.e. whether spectral flatness $S_F$ is greater than or equal to the threshold) based on the first sound signal to which low-pass filter 23*c* is applied. The validity of application of such low-pass filter 23*c* will be described below with reference to waveforms of spectral flatness $S_F$.

Figure 10:
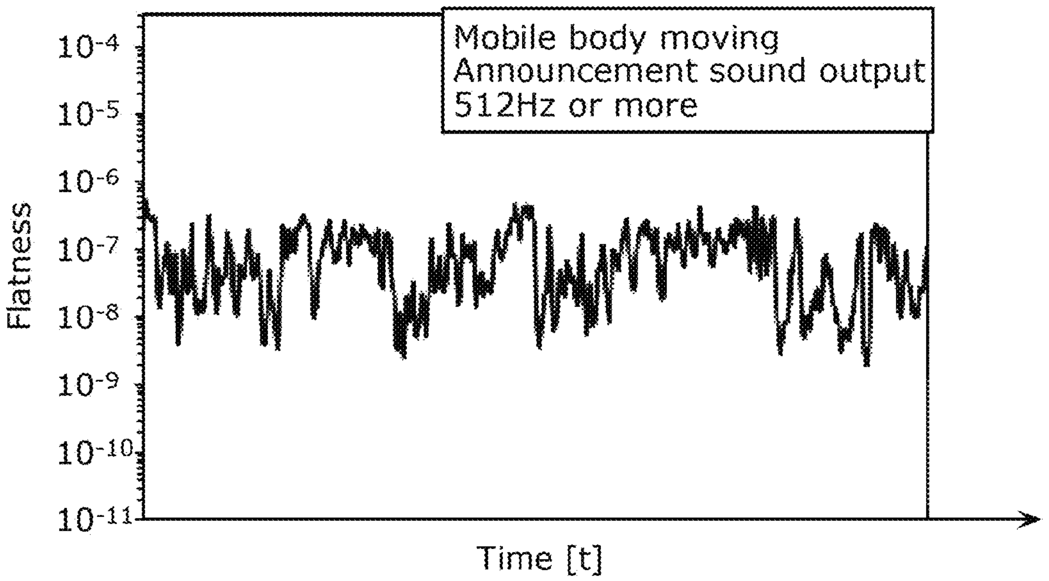
FIG. 10 is a first diagram illustrating temporal changes in spectral flatness.

FIG. 10 is a diagram illustrating temporal changes in spectral flatness $S_F$ in the case where, when the mobile body is moving and an announcement sound is output in the mobile body, spectral flatness $S_F$ is calculated for a component of 512 Hz or more in the first sound signal obtained by microphone 21.

Figure 11:
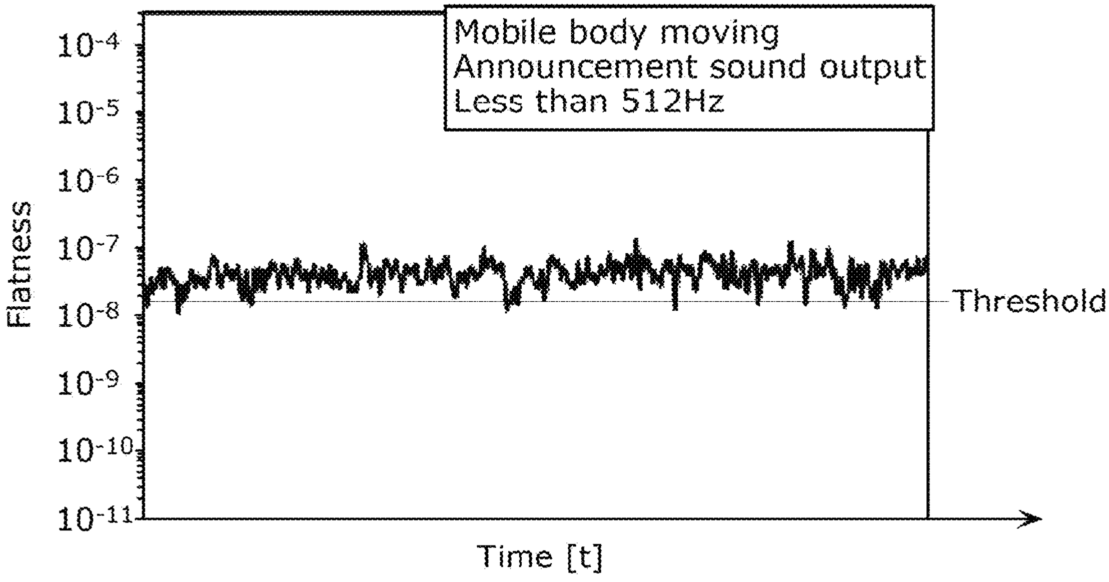
FIG. 11 is a second diagram illustrating temporal changes in spectral flatness.

FIG. 11 is a diagram illustrating temporal changes in spectral flatness $S_F$ in the case where, when the mobile body is moving and an announcement sound is output in the mobile body, spectral flatness $S_F$ is calculated for a component of less than 512 Hz in the first sound signal obtained by microphone 21.

Figure 12:
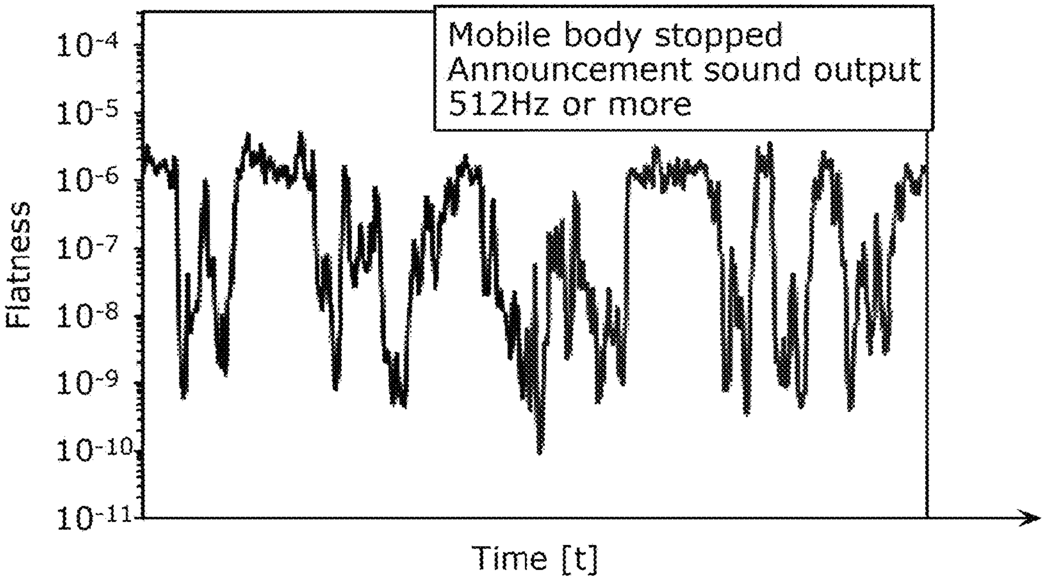
FIG. 12 is a third diagram illustrating temporal changes in spectral flatness.

FIG. 12 is a diagram illustrating temporal changes in spectral flatness $S_F$ in the case where, when the mobile body is stopped and an announcement sound is output in the mobile body, spectral flatness $S_F$ is calculated for a component of 512 Hz or more in the first sound signal obtained by microphone 21.

Figure 13:
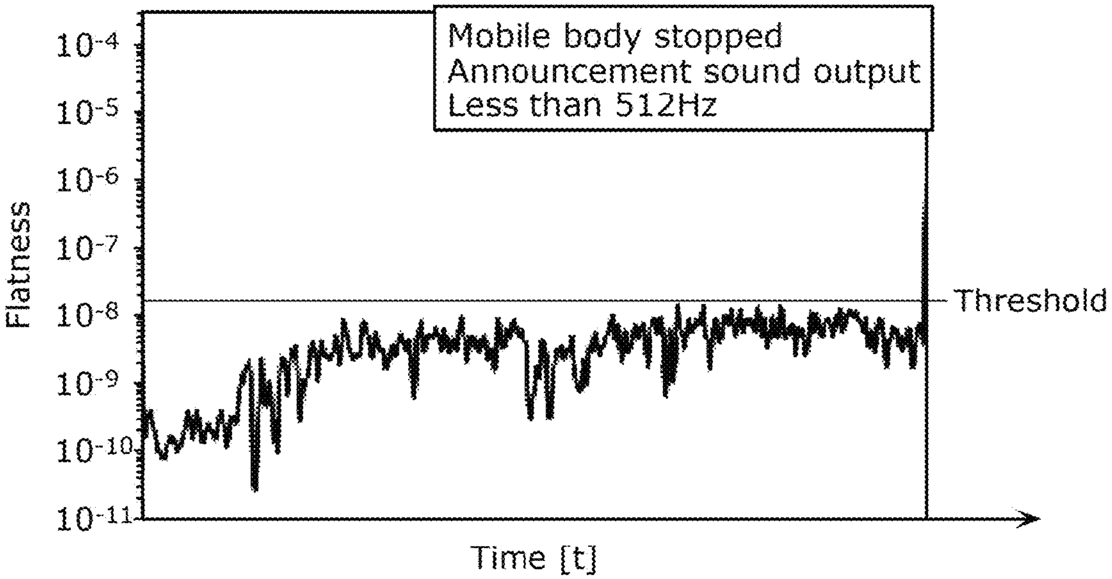
FIG. 13 is a fourth diagram illustrating temporal changes in spectral flatness.

FIG. 13 is a diagram illustrating temporal changes in spectral flatness $S_F$ in the case where, when the mobile body is stopped and an announcement sound is output in the mobile body, spectral flatness $S_F$ is calculated for a component of less than 512 Hz in the first sound signal obtained by microphone 21.

As illustrated in FIG. 10 and FIG. 12, spectral flatness $S_F$ calculated based on a component of 512 Hz or more in the first sound signal varies greatly, and is not suitable for determination of whether the mobile body is moving (i.e. whether spectral flatness $S_F$ is greater than or equal to the threshold).

As illustrated in FIG. 11 and FIG. 13, spectral flatness $S_F$ calculated based on a component of less than 512 Hz in the first sound signal varies little relatively, and is suitable for determination of whether the mobile body is moving (i.e. whether spectral flatness $S_F$ is greater than or equal to the threshold). Hence, by determining whether the mobile body is moving (i.e. whether spectral flatness $S_F$ is greater than or equal to the threshold) based on the first sound signal to which low-pass filter 23*c* is applied, the determination accuracy can be improved.

In the examples in FIG. 11 and FIG. 13, if the threshold is set to around $10^{-8}$, determiner 24*c* can determine whether the mobile body is moving or stopped. Such a threshold is an example, and the threshold may be determined empirically or experimentally by a designer.

Determiner 24*c* may determine whether the noise satisfies the predetermined requirement based on whether the moving average value or moving median value of spectral flatness $S_F$ is greater than or equal to a threshold. The threshold in this case is set to a value corresponding to the moving average value or moving median value.

[Supplementary Remarks on Determination of Whether Sound Contains Human Voice]

In the foregoing embodiment, determiner 24*c* determines whether the sound obtained by microphone 21 contains human voice based on the first sound signal to which high-pass filter 23*b* is applied. The validity of application of such high-pass filter 23*b* will be described below with reference to spectrograms.

Figure 14:
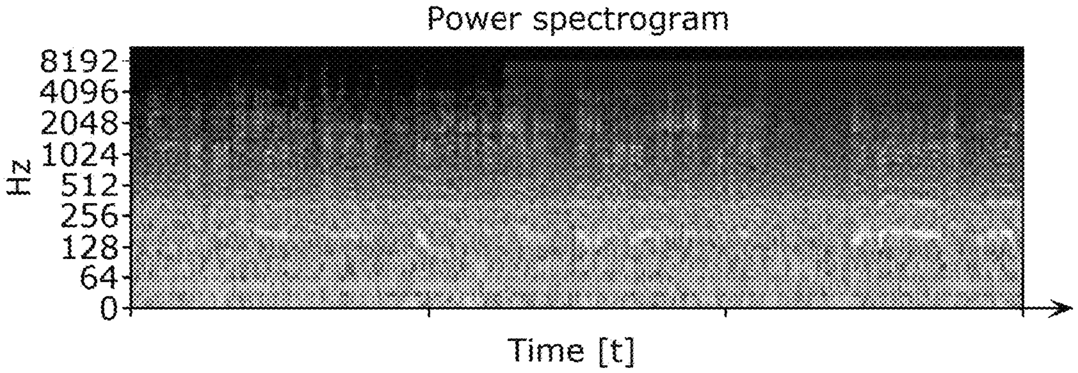
FIG. 14 is a first diagram illustrating a spectrogram of a first sound signal.
Figure 15:
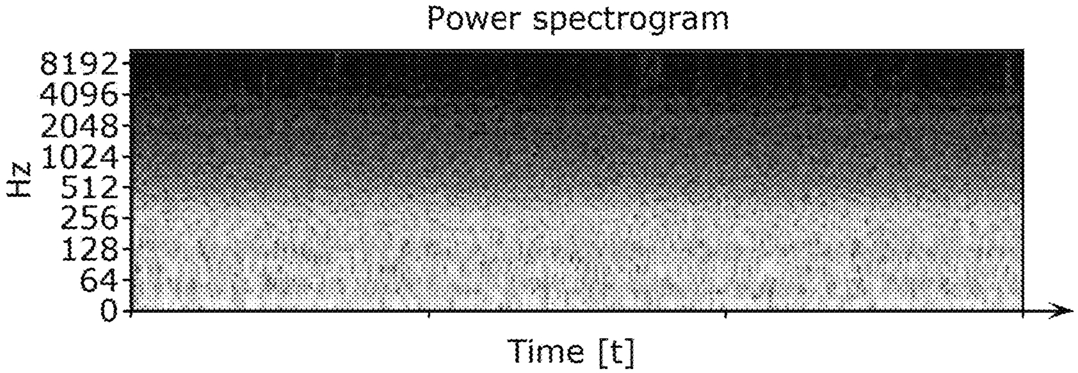
FIG. 15 is a second diagram illustrating a spectrogram of a first sound signal.

FIG. 14 is a diagram illustrating the spectrogram of the first sound signal obtained by microphone 21 when the mobile body is moving and an announcement sound is output in the mobile body. FIG. 15 is a diagram illustrating the spectrogram of the first sound signal obtained by microphone 21 when the mobile body is moving and an announcement sound is not output in the mobile body.

Figure 16:
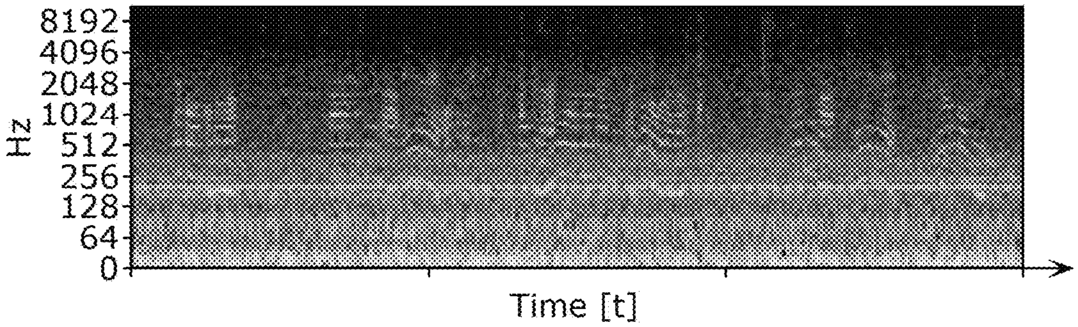
FIG. 16 is a third diagram illustrating a spectrogram of a first sound signal.
Figure 17:
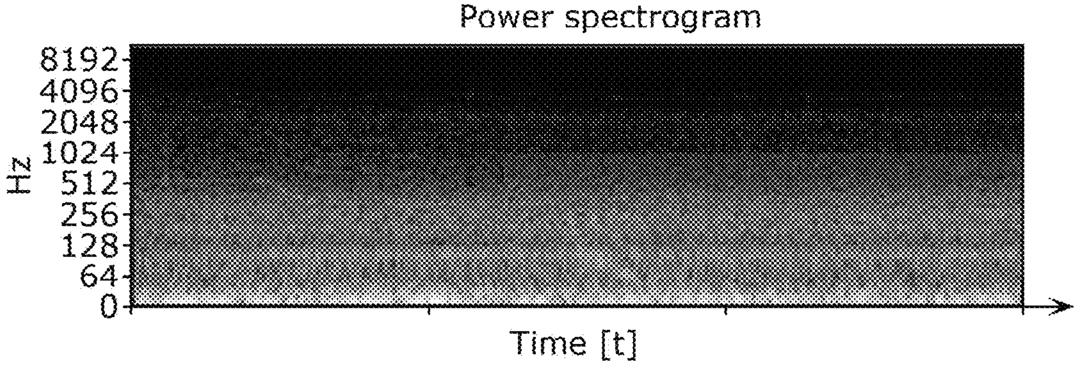
FIG. 17 is a fourth diagram illustrating a spectrogram of a first sound signal.

FIG. 16 is a diagram illustrating the spectrogram of the first sound signal obtained by microphone 21 when the mobile body is stopped and an announcement sound is output in the mobile body. FIG. 17 is a diagram illustrating the spectrogram of the first sound signal obtained by microphone 21 when the mobile body is stopped and an announcement sound is not output in the mobile body.

In FIG. 14 to FIG. 17, whiter parts have higher power values, and blacker parts have lower power values. As illustrated in FIG. 14 to FIG. 17, when an announcement sound is output (FIG. 14 and FIG. 16), a wave pattern corresponding to human voice appears in a band of 512 Hz or more regardless of whether the mobile body is moving or stopped. Accordingly, determiner 24*c* can determine whether the sound obtained by microphone 21 contains human voice, based on at least a component of 512 Hz or more in the first sound signal. As a result of determiner 24*c* determining whether the sound obtained by microphone 21 contains human voice based on the first sound signal to which high-pass filter 23*b* is applied, the determination accuracy can be improved.

[Variations of Noise Removal Filter]

Figure 18:
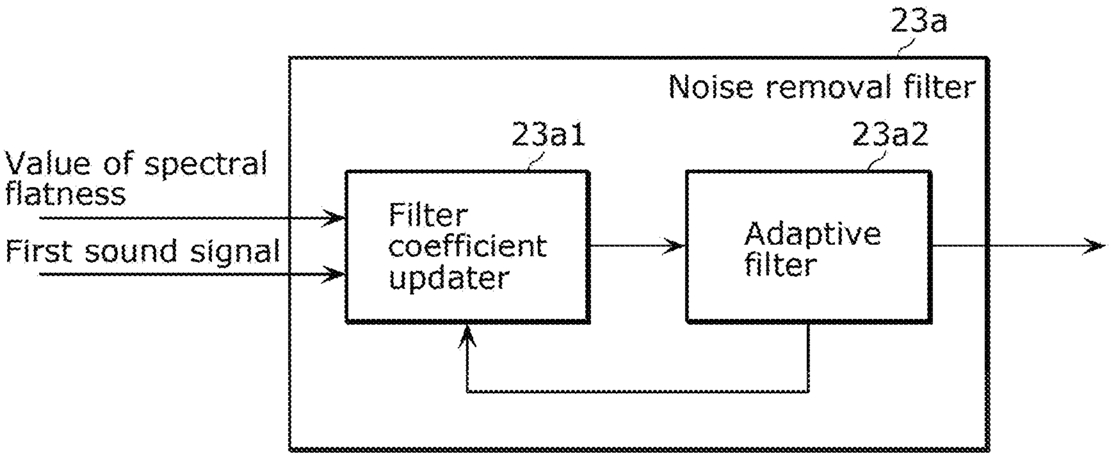
FIG. 18 is a block diagram illustrating the functional structure of a noise removal filter which functions as an adaptive filter.

Noise removal filter 23*a* may be an adaptive filter. Specifically, noise removal filter 23*a* may update a filter coefficient using the value of spectral flatness $S_F$ output from noise feature value calculator 24*b*, as indicated by the dashed arrow from noise feature value calculator 24*b* to noise removal filter 23*a* in FIG. 2. FIG. 18 is a block diagram illustrating the functional structure of noise removal filter 23*a* that functions as an adaptive filter.

As illustrated in FIG. 18, noise removal filter 23*a* as an adaptive filter includes filter coefficient updater 23*a*1 and adaptive filter 23*a*2.

Filter coefficient updater 23*a*1 sequentially updates the coefficient of the adaptive filter based on the following update formula. In the following formula, w is the filter coefficient, x is the first sound signal, and e is an error signal. The error signal is a signal corresponding to the difference between the first sound signal to which the filter coefficient has been applied and a target signal. μ is a parameter (hereinafter also referred to as "step size parameter") indicating the update amount (step size) of the filter coefficient, and is a positive coefficient.

$$w(n+1)=w(n)+\mu e(n)x(n) \quad \text{[Math. 2]}$$

Adaptive filter 23*a*2 applies, to the first sound signal, a filter formed by the filter coefficient calculated by filter coefficient updater 23*a*1, and outputs, to high-pass filter 23*b*, the first sound signal (i.e. noise-removed first sound signal) to which the filter coefficient has been applied.

Filter coefficient updater 23*a*1 may change the step size parameter using the value of spectral flatness $S_F$. For example, filter coefficient updater 23*a*1 changes the step size parameter to be larger than the current value when the value of spectral flatness $S_F$ is larger. Specifically, filter coefficient updater 23_a_1 changes the step size parameter using a first threshold and a second threshold greater than the first threshold in the following manner.

In the case where the value of spectral flatness $S_F$ is less than the first threshold, filter coefficient updater 23_a_1 changes the step size parameter to be smaller than the current value. In the case where the value of spectral flatness $S_F$ is greater than or equal to the first threshold and less than the second threshold, filter coefficient updater 23_a_1 maintains the current value of the step size parameter. In the case where the value of spectral flatness $S_F$ is greater than or equal to the second threshold, filter coefficient updater 23_a_1 changes the step size parameter to be larger than the current value.

In this way, noise removal filter 23_a_ (filter coefficient updater 23_a_1) can facilitate adaptive learning when noise is closer to white noise. Filter coefficient updater 23_a_1 need not change the step size parameter in the external sound capture mode. That is, filter coefficient updater 23_a_1 may fix the step size parameter at a certain value in the external sound capture mode.

Although noise removal filter 23_a_ is implemented as a feedforward control type adaptive filter using the first sound signal output from microphone 21 in the example illustrated in FIG. 18, noise removal filter 23_a_ may be implemented as a feedback control type adaptive filter.

Noise removal filter 23_a_ is not limited to a filter whose coefficient is fixed or an adaptive filter. Noise removal filter 23_a_ may be a filter that includes a plurality of filters of different types and is capable of switching between the plurality of filters based on the value of spectral flatness $S_F$.

Effects, Etc.

As described above, ear-worn device 20 includes: microphone 21 that obtains a sound and outputs a first sound signal of the sound obtained; DSP 22 that outputs a second sound signal based on the first sound signal, when determining that the sound satisfies a predetermined requirement relating to a noise component contained in the sound and the sound contains human voice; loudspeaker 28 that outputs a reproduced sound based on the second sound signal output; and housing 29 that contains microphone 21, DSP 22, and loudspeaker 28. DSP 22 is an example of a signal processing circuit.

Such ear-worn device 20 can reproduce human voice heard in the surroundings according to the ambient noise environment. For example, when an announcement sound is output in a mobile body while the mobile body is moving, ear-worn device 20 can output a reproduced sound including the announcement sound from loudspeaker 28.

For example, DSP 22 outputs the first sound signal as the second sound signal, when determining that the sound satisfies the predetermined requirement and the sound contains human voice.

Such ear-worn device 20 can reproduce human voice heard in the surroundings based on the first sound signal.

For example, DSP 22 outputs the second sound signal obtained by performing signal processing on the first sound signal, when determining that the sound satisfies the predetermined requirement and the sound contains human voice.

Such ear-worn device 20 can reproduce human voice heard in the surroundings based on the first sound signal that has undergone the signal processing.

For example, the signal processing includes equalizing processing for enhancing a specific frequency component of the sound.

Such ear-worn device 20 can enhance and reproduce human voice heard in the surroundings.

For example, DSP 22 causes loudspeaker 28 not to output the reproduced sound based on the second sound signal, when determining that the sound does not satisfy the predetermined requirement and when determining that the sound does not contain human voice.

Such ear-worn device 20 can stop the output of the reproduced sound based on the second sound signal, for example in the case where no human voice is heard in the surroundings.

For example, DSP 22 outputs a third sound signal obtained by performing phase inversion processing on the first sound signal, when determining that the sound does not satisfy the predetermined requirement and when determining that the sound does not contain human voice, and loudspeaker 28 outputs a reproduced sound based on the third sound signal output.

Such ear-worn device 20 can make ambient sound less audible, for example in the case where no human voice is heard in the surroundings.

For example, ear-worn device 20 further includes: mixing circuit 27_b_ that mixes the second sound signal output with a fourth sound signal provided from a sound source. After DSP 22 starts outputting the second sound signal, mixing circuit 27_b_ mixes the second sound signal with the fourth sound signal attenuated in amplitude to be lower than before DSP 22 starts outputting the second sound signal.

Such ear-worn device 20 can enhance and reproduce human voice heard in the surroundings.

For example, DSP 22: determines whether the sound satisfies the predetermined requirement, based on the first sound signal to which low-pass filter 23_c_ is applied; and determines whether the sound contains human voice, based on the first sound signal to which high-pass filter 23_b_ is applied.

Such ear-worn device 20 can improve the determination accuracy by applying the filters to the first sound signal.

For example, DSP 22: determines whether the sound contains human voice, based on the first sound signal to which an adaptive filter is applied; and changes an update amount of a filter coefficient of the adaptive filter, based on noise contained in the sound.

Such ear-worn device 20 can vary the effect of the adaptive filter according to the ambient noise environment.

For example, the sound contains a first sound obtained in a first period and a second sound obtained in a second period after the first period. DSP 22 outputs the second sound signal, when determining that the first sound satisfies the predetermined requirement, the first sound does not contain human voice, and the second sound contains human voice.

Such ear-worn device 20 can improve the accuracy of determination of whether the sound satisfies the predetermined requirement.

A reproduction method executed by a computer such as DSP 22 includes: output step S16_a_ (or S16_d_) of outputting a second sound signal based on a first sound signal of a sound, when determining, based on the first sound signal, that the sound satisfies a predetermined requirement relating to a noise component contained in the sound and the sound contains human voice, the first sound signal being output from microphone 21 that obtains the sound; and reproduction step S16*c* (or S16*f*) of outputting a reproduced sound from loudspeaker 28 based on the second sound signal output.

Such a reproduction method can reproduce human voice heard in the surroundings according to the ambient noise environment.

Other Embodiments

While the embodiment has been described above, the present disclosure is not limited to the foregoing embodiment.

For example, although the foregoing embodiment describes the case where the ear-worn device is an earphone-type device, the ear-worn device may be a headphone-type device. Although the foregoing embodiment describes the case where the ear-worn device has the function of reproducing music content, the ear-worn device may not have the function (the communication circuit and the mixing circuit) of reproducing music content. For example, the ear-worn device may be an earplug or a hearing aid having the noise canceling function and the external sound capture function.

Although the foregoing embodiment describes the case where a machine learning model is used to determine whether the sound obtained by the microphone contains human voice, the determination may be made based on another algorithm without using a machine learning model, such as speech feature value pattern matching. Although the foregoing embodiment describes the case where spectral flatness is used to determine whether the sound obtained by the microphone satisfies the predetermined requirement relating to the noise component contained in the sound, the determination may be made using a machine learning model.

Although the foregoing embodiment describes the case where the predetermined requirement relating to the noise component is a requirement corresponding to whether the mobile body is moving, the predetermined requirement relating to the noise component may be any other requirement such as a requirement corresponding to whether the ambient noise level is higher than a predetermined value.

The structure of the ear-worn device according to the foregoing embodiment is an example. For example, the ear-worn device may include structural elements not illustrated, such as a D/A converter, a filter, a power amplifier, and an A/D converter.

Although the foregoing embodiment describes the case where the sound signal processing system is implemented by a plurality of devices, the sound signal processing system may be implemented as a single device. In the case where the sound signal processing system is implemented by a plurality of devices, the functional structural elements in the sound signal processing system may be allocated to the plurality of devices in any way. For example, all or part of the functional structural elements included in the ear-worn device in the foregoing embodiment may be included in the mobile terminal.

The method of communication between the devices in the foregoing embodiment is not limited. In the case where the two devices communicate with each other in the foregoing embodiment, a relay device (not illustrated) may be located between the two devices.

The orders of processes described in the foregoing embodiment are merely examples. A plurality of processes may be changed in order, and a plurality of processes may be performed in parallel. A process performed by any specific processing unit may be performed by another processing unit. Part of digital signal processing described in the foregoing embodiment may be realized by analog signal processing.

Each of the structural elements in the foregoing embodiment may be implemented by executing a software program suitable for the structural element. Each of the structural elements may be implemented by means of a program executing unit, such as a CPU or a processor, reading and executing the software program recorded on a recording medium such as a hard disk or semiconductor memory.

Each of the structural elements may be implemented by hardware. For example, the structural elements may be circuits (or integrated circuits). These circuits may constitute one circuit as a whole, or may be separate circuits. These circuits may each be a general-purpose circuit or a dedicated circuit.

The general or specific aspects of the present disclosure may be implemented using a system, a device, a method, an integrated circuit, a computer program, or a computer-readable recording medium such as CD-ROM, or any combination of systems, devices, methods, integrated circuits, computer programs, and recording media. For example, the presently disclosed techniques may be implemented as a reproduction method executed by a computer such as an ear-worn device or a mobile terminal, or implemented as a program for causing the computer to execute the reproduction method. The presently disclosed techniques may be implemented as a computer-readable non-transitory recording medium having the program recorded thereon. The program herein includes an application program for causing a general-purpose mobile terminal to function as the mobile terminal in the foregoing embodiment.

Other modifications obtained by applying various changes conceivable by a person skilled in the art to each embodiment and any combinations of the structural elements and functions in each embodiment without departing from the scope of the present disclosure are also included in the present disclosure.

INDUSTRIAL APPLICABILITY

The ear-worn device according to the present disclosure can output a reproduced sound containing human voice in the surroundings, according to the ambient noise environment.

REFERENCE SIGNS LIST

- 10 sound signal processing system
- 20 ear-worn device
- 21 microphone
- 22 DSP
- 23 filter
- 23*a* noise removal filter
- 23*a*1 filter coefficient updater
- 23*a*2 adaptive filter
- 23*b* high-pass filter
- 23*c* low-pass filter
- 24 signal processor
- 24*a* speech feature value calculator
- 24*b* noise feature value calculator
- 24*c* determiner
- 24*d* switch
- 26 memory
- 27*a* communication circuit
- 27*b* mixing circuit
- 28 loudspeaker 29 housing
30 mobile terminal
31 UI
32 communication circuit
33 CPU
34 memory

The invention claimed is:

1. An ear-worn device comprising:
a microphone that obtains a sound and outputs a first sound signal of the sound obtained;
a signal processing circuit that
outputs a second sound signal based on the first sound signal, when determining that the sound satisfies a predetermined requirement relating to a noise component contained in the sound and the sound contains human voice, and
outputs a third sound signal obtained by performing phase inversion processing on the first sound signal, when determining that the sound does not satisfy the predetermined requirement and when determining that the sound does not contain human voice;
a loudspeaker that outputs a reproduced sound based on the second sound signal output or on the third sound signal output; and
a housing that contains the microphone, the signal processing circuit, and the loudspeaker.

2. The ear-worn device according to claim 1,
wherein the signal processing circuit outputs the first sound signal as the second sound signal, when determining that the sound satisfies the predetermined requirement and the sound contains human voice.

3. The ear-worn device according to claim 1,
wherein the signal processing circuit outputs the second sound signal obtained by performing signal processing on the first sound signal, when determining that the sound satisfies the predetermined requirement and the sound contains human voice.

4. The ear-worn device according to claim 3,
wherein the signal processing includes equalizing processing for enhancing a specific frequency component of the sound.

5. The ear-worn device according to claim 1,
wherein the signal processing circuit causes the loudspeaker not to output the reproduced sound based on the second sound signal, when determining that the sound does not satisfy the predetermined requirement and when determining that the sound does not contain human voice.

6. The ear-worn device according to claim 1, further comprising:
a mixing circuit that mixes the second sound signal output with a fourth sound signal provided from a sound source,
wherein after the signal processing circuit starts outputting the second sound signal, the mixing circuit mixes the second sound signal with the fourth sound signal attenuated in amplitude to be lower than before the signal processing circuit starts outputting the second sound signal.

7. The ear-worn device according to claim 1,
wherein the signal processing circuit:
determines whether the sound contains human voice, based on the first sound signal to which an adaptive filter is applied; and
changes an update amount of a filter coefficient of the adaptive filter, based on noise contained in the sound.

8. The ear-worn device according to claim 1,
wherein the sound contains a first sound obtained in a first period and a second sound obtained in a second period after the first period, and
the signal processing circuit outputs the second sound signal, when determining that the first sound satisfies the predetermined requirement, the first sound does not contain human voice, and the second sound contains human voice.

9. The ear-worn device according to claim 1,
wherein the predetermined requirement is a requirement corresponding to whether a mobile body is moving, or a requirement corresponding to whether an ambient noise level is higher than a predetermined value.

10. An ear-worn device comprising:
a microphone that obtains a sound and outputs a first sound signal of the sound obtained;
a signal processing circuit that outputs a second sound signal based on the first sound signal, when determining that the sound satisfies a predetermined requirement relating to a noise component contained in the sound and the sound contains human voice;
a loudspeaker that outputs a reproduced sound based on the second sound signal output; and
a housing that contains the microphone, the signal processing circuit, and the loudspeaker
wherein the signal processing circuit:
determines whether the sound satisfies the predetermined requirement, based on the first sound signal to which a low-pass filter is applied; and
determines whether the sound contains human voice, based on the first sound signal to which a high-pass filter is applied.

11. The ear-worn device according to claim 10,
wherein the predetermined requirement is a requirement corresponding to whether a mobile body is moving, or a requirement corresponding to whether an ambient noise level is higher than a predetermined value.

12. A reproduction method comprising:
outputting a second sound signal based on a first sound signal of a sound, when determining, based on the first sound signal, that the sound satisfies a predetermined requirement relating to a noise component contained in the sound and the sound contains human voice, the first sound signal being output from a microphone that obtains the sound, or
outputting a third sound signal obtained by performing phase inversion processing on the first sound signal, when determining that the sound does not satisfy the predetermined requirement and when determining that the sound does not contain human voice; and
outputting a reproduced sound from a loudspeaker based on the second sound signal output or on the third sound signal output.

13. A computer-readable non-transitory recording medium having recorded thereon a program for causing a computer to execute the reproduction method according to claim 12.

14. The reproduction method according to claim 12,
wherein the predetermined requirement is a requirement corresponding to whether a mobile body is moving, or a requirement corresponding to whether an ambient noise level is higher than a predetermined value.

* * * * *